United States Patent [19]

Millar

[11] Patent Number: 5,431,628
[45] Date of Patent: Jul. 11, 1995

[54] PRESSURE-SENSING DIAGNOSTIC CATHETER

[75] Inventor: Huntly D. Millar, Houston, Tex.

[73] Assignee: Millar Instruments, Inc., Houston, Tex.

[21] Appl. No.: 192,953

[22] Filed: Feb. 7, 1994

Related U.S. Application Data

[63] Continuation of Ser. No. 954,360, Sep. 29, 1992, abandoned.

[51] Int. Cl.⁶ .............................................. A61M 29/00
[52] U.S. Cl. ............................... 604/100; 128/662.04; 128/662.06
[58] Field of Search ..................... 604/96–100; 128/660.02, 662.04, 662.06, 673, 675, 748 (U.S. only); 73/714

[56] References Cited

U.S. PATENT DOCUMENTS

| | | | |
|---|---|---|---|
| 4,274,423 | 6/1981 | Mizuno et al. | 128/675 |
| 4,665,925 | 5/1987 | Millar | 128/663 |
| 4,722,348 | 2/1988 | Ligtenberg | 128/675 |
| 4,733,669 | 3/1988 | Segal | 128/662.04 |
| 4,771,782 | 9/1988 | Millar | 128/748 |
| 4,878,898 | 11/1989 | Griffin et al. | 128/675 |
| 4,924,877 | 5/1990 | Brooks | 128/673 |

OTHER PUBLICATIONS

McDermott, et al. "Monitoring Acute Compartment Pressures with S.T.I.C. Catheter," *Clinical Orthopaedics and Related Research*, 190:192–198, 1984.

*Primary Examiner*—Jerome L. Kruter
*Attorney, Agent, or Firm*—Arnold, White & Durkee

[57] ABSTRACT

The invention relates to catheters having a distally-mounted balloon and pressure sensor and to methods of placing such catheters within physiological vessels. Catheters have a central lumen extending through the catheter and a pressure sensor which lies within the distal portion of the central lumen but does not occlude the lumen. Additionally, catheters may have a Doppler velocity measurement sensor affixed to the distal end of the catheter for measuring fluid velocity distal to the catheter. Inflation of the balloon prevents vessel wall contact with other portions of the catheter tip during flow-directed placement of the catheter. During catheter placement to obtain a wedge pressure, the balloon is inflated until fluid velocity detected with the Doppler sensor is substantially zero.

12 Claims, 2 Drawing Sheets

PRESSURE-SENSING DIAGNOSTIC CATHETER

This application is a continuation of application Ser. No. 07/954,360, filed Sep. 29, 1992, now abandoned.

BACKGROUND OF THE INVENTION

Field of the Invention

The invention relates to catheters having a distally-mounted balloon and pressure sensor and to methods of placing such catheters within the body of a patient for medical diagnosis and treatment.

Balloon Tip Catheters

Medical diagnosis and treatment sometimes requires determination of pressures within a physiological vessel or cavity (e.g., a blood vessel) in which there is fluid but in which fluid flow has been stopped. Fluid flow in a vessel may be temporarily stopped if the vessel is occluded by inflating a balloon attached to a catheter tip placed within the lumen of the vessel (i.e., wedging the balloon within the vessel). The resulting occlusion pressure or wedge pressure (e.g., a pulmonary wedge pressure) may reflect conditions downstream from the wedged balloon in locations which are otherwise difficult to reach with pressure-sensing catheters.

In addition to its use for occluding vessels when a wedge pressure is desired, a balloon attached to a catheter tip may also be used to aid in placement of a catheter in a flowing fluid stream. For example, if a balloon-tip catheter is introduced into the right atrium of a patient and the balloon is then inflated, blood flow will tend to carry the balloon with its attached catheter into the right ventricle and then into the pulmonary artery and one of the branches thereof. Such flow direction is commonly used to help in placing catheters for wedge pressure measurements, but may be used more generally to aid in threading catheters from upstream portions of a fluid stream to downstream portions.

Catheter Placement Problems

Because catheters are often designed to be pushed into various physiological vessels, they must have sufficient stiffness to avoid collapse under the axial compressive load generated during placement. Such stiffness, while useful for threading a catheter through a vessel wall and any overlying tissue, may cause the catheter tip to excite or damage anatomic structures it contacts after entering the vessel. A common site for such problems to arise is the right ventricle of the heart, where even light catheter-wall contact may precipitate cardiac dysrhythmias, and strong contact may penetrate the ventricular wall. Such potentially damaging tip contact can be reduced or even eliminated through inflation of a balloon which generally surrounds the tip and reduces its contact with the walls of vessels in which the catheter is placed. As noted above, inflation of the tip balloon also tends to cause the catheter to be carried along with the flow of fluid in the vessel. Thus, while flow-directed balloon-tip catheters have considerable utility, care must be taken that the balloon completely shields the tip when inflated. Any protrusion beyond the tip, as by a tip-mounted pressure sensor, raises the possibility of undesirable wall contact during catheter placement.

Another potential problem with balloon-tip catheters concerns the possibility of vessel damage which may arise if the balloon is overinflated while within the vessel. Ideally, the balloon would be inflated just enough to contact the vessel walls and occlude the vessel completely. The desired condition is that there be no fluid flow past the balloon, but that inflation beyond that point be avoided. Unfortunately, small leaks of fluid past the balloon tend to generate small pressure signals in the fluid distal to the balloon. If a fluid-filled lumen is used to communicate such pressure changes to pressure transducers at the proximal end of the catheter, small pressure signals may be lost because they are easily distorted by slight disturbances of the fluid column transmitting the pressures. Due to the difficulty of interpreting small pressure signals in catheters with proximal transducers, balloons on these catheters may be either over- or underinflated, with the first condition increasing the risk of vessel damage and the second condition degrading the quality of wedge pressures obtained.

Signal-to-Noise Ratios in Wedge Pressures

Physiological wedge pressures are often comparatively low, producing weak signals relative to the sources of error and distortion in fluid filled catheter transducer systems. Further, catheters intended to be flow directed must be relatively soft and highly compliant to be responsive to flow-generated forces and follow the course of the flow. Softness and high compliance, on the other hand, are associated with increased motion artifacts in fluid filled catheters. Thus, fluid filled, flow directed catheters are not well suited for obtaining high-fidelity pressure readings because of the relatively low signal-to-noise ratios obtainable with them. In contrast, catheters having pressure sensors at the tip (distal to the balloon) produce cleaner signals which are comparatively artifact-free. The distal pressure sensors, however, tend to protrude beyond the inflated balloon and thus may have a potential for causing cardiac dysrhythmias similar to that of a catheter with the balloon deflated.

SUMMARY OF THE INVENTION

The present invention relates to improvements in diagnostic catheters which reduce or eliminate the problems described above. Catheters of the present invention demonstrate several advantages, among them being: a higher signal-to-noise ratio than generally available from fluid-filled catheters; a lower potential for tip-impact damage or dysrhythmia generation than obtainable with conventional pressure transducer-tipped catheters; and improved methods of use, including a superior capability to aid balloon adjustment for optimal wedging.

These advantages arise from use of a distal pressure transducer which resides within and partially occupies a catheter lumen extending from the distal catheter tip to a proximal connector port. Because they retain a lumen open to the distal tip, catheters of the present invention retain the advantages whereby fluids may be withdrawn or added after the balloon is inflated. For example, a low-flow heparin drip may be maintained through the catheter and over the pressure sensor to avoid blood clots in the catheter tip near the sensor. In addition, other diagnostic or therapeutic instruments may be introduced through the lumen to the vessel area distal to the balloon.

Other advantages of flow directed (balloon tip) catheters of the present invention result from Doppler velocity sensing with an annular crystal attached to the distal catheter tip. The velocity sensing function may be combined with additional Doppler sensors on the catheter or external ultrasound imaging devices to measure both vessel area and flow velocity, thus allowing calculation of instantaneous fluid flow rates. Measured in the pulmonary artery, such flow rates would represent instantaneous cardiac output measurements.

In another application of the invention, fluid flow around the balloon and past the catheter tip is detected by the Doppler velocity sensor during balloon inflation. The balloon may then be inflated just to the point where flow is totally obstructed and sensed velocity decreases to zero. Balloon inflation by this procedure avoids both damage to the physiological wall due to overinflation and inaccurate downstream pressure determinations due to fluid leakage past the balloon.

A first preferred embodiment of the present invention is a catheter to measure pressure in a fluid-carrying vessel and to occlude the vessel, the catheter comprising: an elongated, flexible, tubular body having a proximal end, a distal end, and a circumference, adapted for partial insertion into a vessel; a vessel occluding balloon sealingly attached to the circumference of the catheter adjacent the distal end; a central lumen extending through at least a portion of the tubular body from a proximal location substantially to the distal end; a balloon inflation lumen extending from a proximal location through at least a portion of the tubular body and communicating with the balloon for inflating and deflating the balloon; a pressure sensor disposed within the central lumen, said lumen remaining open to fluid flow, and said sensor having an ambient pressure port and being adjacent the distal end; and an ambient pressure lumen extending from a proximal location through at least a portion of the tubular body and communicating with the sensor ambient pressure port. The pressure sensor may comprise a flexible pressure-sensing diaphragm and may additionally comprise a plurality of strain gauges communicating with the pressure-sensing diaphragm.

The above catheter may additionally comprise Doppler means for measuring velocity of fluid adjacent the distal end, and the means may be disposed on the distal end of the tubular body. Further, the means may comprise a washer-shaped ultrasonic transducer.

A second preferred embodiment of the present invention is a method for obtaining a wedge pressure in a vessel, the method comprising: positioning a distal portion of the catheter of the first embodiment within a vessel; measuring the velocity of fluid within the vessel distal to the catheter; inflating the balloon until said measured velocity of fluid within the vessel distal to the catheter is substantially zero; occluding the central lumen proximal to the location of the pressure sensor; and determining the wedge pressure at the pressure sensor.

A third preferred embodiment of the present invention is a method for measuring flow rate in a vessel, the method comprising: positioning a distal portion of the catheter of the first embodiment within a vessel; measuring a fluid velocity within the vessel by Doppler means; measuring dimensions of the vessel; and calculating flow rate in the vessel from fluid velocity and vessel dimensions. Measuring vessel dimensions may be accomplished by ultrasound means positioned external to the patient or Doppler means attached to the catheter.

DETAILED DESCRIPTION OF THE PREFERRED EMBODIMENTS

Figure 1:
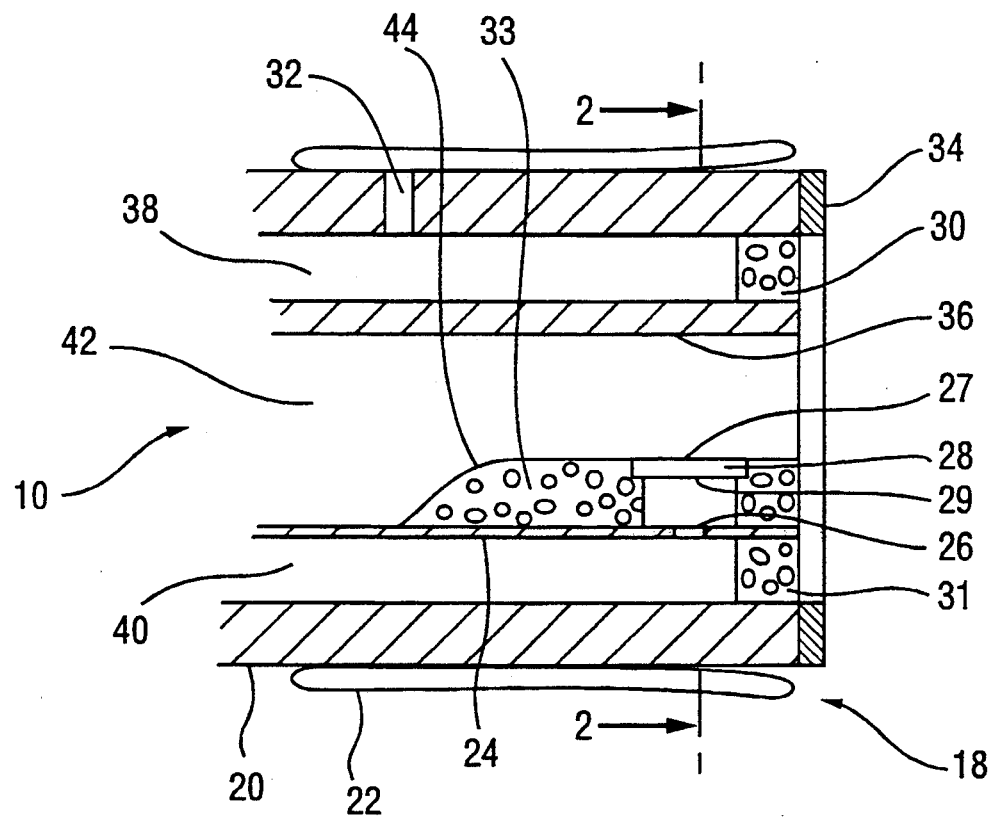
FIG. 1 is a longitudinal cross section of the distal portion of an improved flow-directed catheter in accordance with the present invention.
Figure 2:
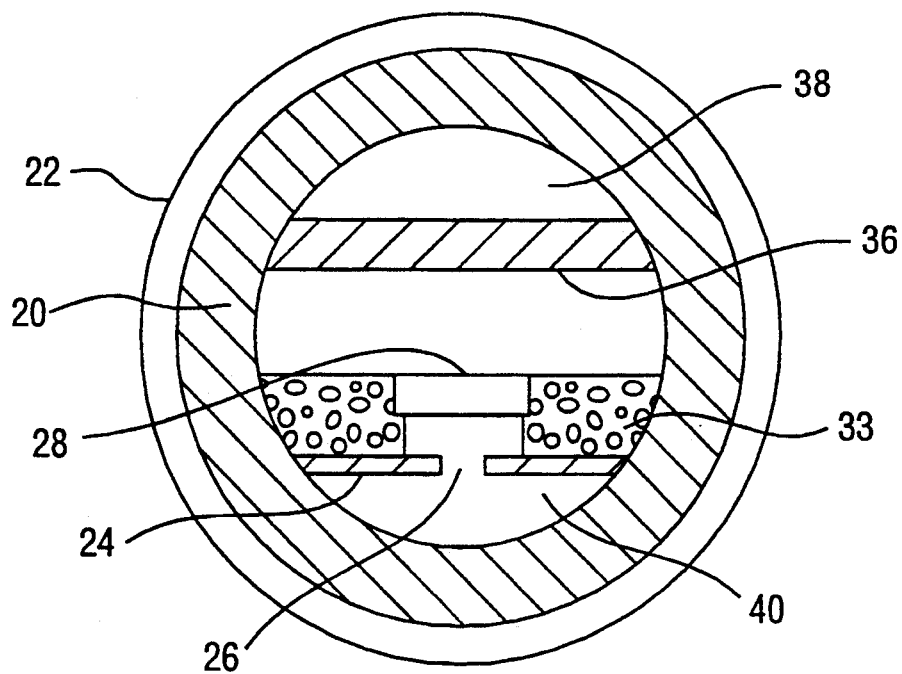
FIG. 2 is a transverse cross section of the portion of catheter shown in FIG. 1.
Figure 3:
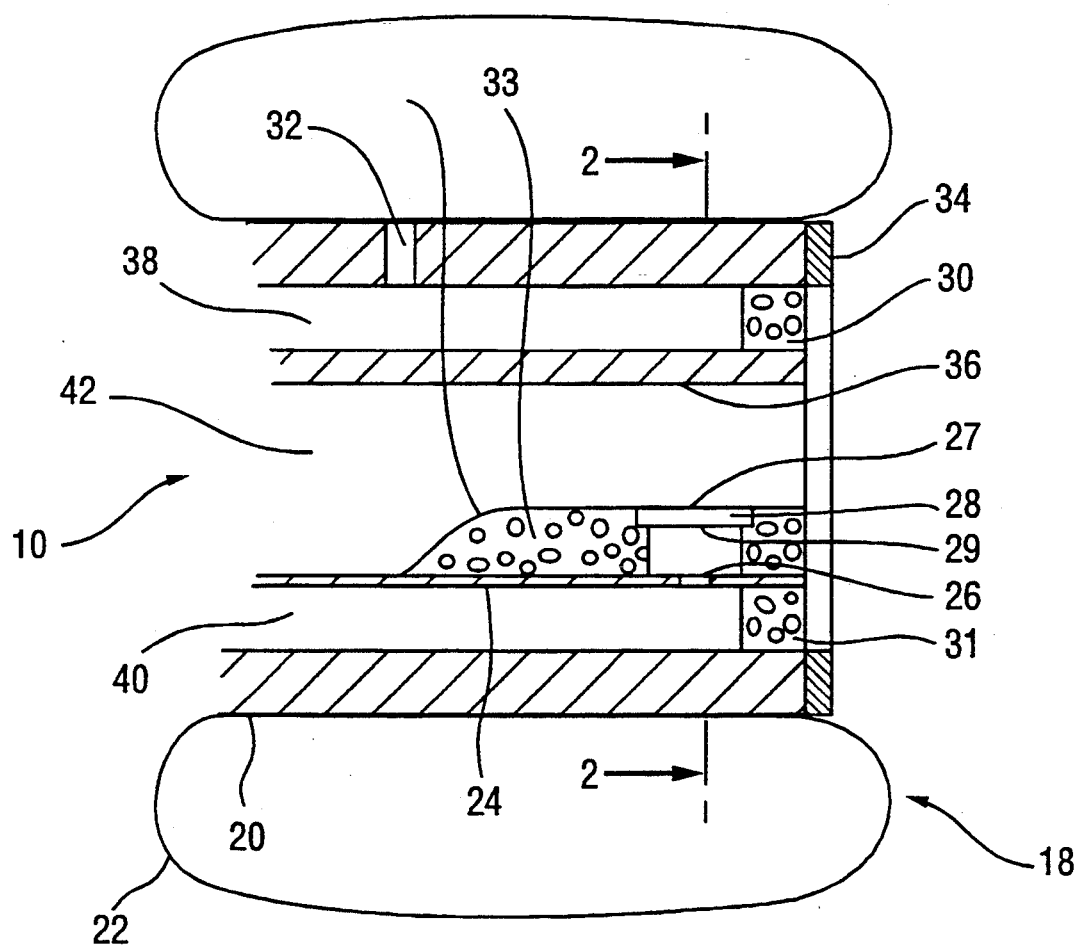
FIG. 3 is a longitudinal cross-section of the distal portion of an improved flow-directed catheter with the balloon in an inflated position, according to the present invention.

Referring to FIGS. 1, 2 and 3, the distal portion 18 of the diagnostic catheter 20 of the present invention is preferably insertable into a vessel. The catheter comprises a balloon inflation lumen 38, a central lumen 42, and an ambient pressure lumen 40. In preferred embodiments, separation of central lumen 42 from balloon inflation lumen 38 is achieved by septum 36, and separation of central lumen 42 from ambient pressure lumen 40 is achieved by septum 24. Those skilled in the art will recognize that catheters of the present invention may have physical arrangements of at least three lumens different from that shown for illustration in FIGS. 1 and 2. In preferred embodiments of the invention, the functional Characteristic of each lumen governs its placement within the catheter, and lumen arrangement may vary from that illustrated in FIGS. 1 and 2. During catheter use, each lumen is accessed from a proximal location 10 on catheter 20.

The balloon inflation lumen 38 communicates through port 32 with the interior of balloon 22 sealingly attached to the circumference of catheter 20 adjacent the distal end 18. The extreme distal portion of lumen 38 is completely occluded by a plug 30 of silicone rubber or similar biocompatible material. The central lumen 42 extends through washer-shaped Doppler ring 34 which is sealingly attached to catheter 20. The ambient pressure lumen 40 communicates through ambient pressure port 26 with the atmospheric side 29 of flexible pressure-sensing diaphragm 28, the air pressure in lumen 40 preferably being atmospheric pressure. The distal end of ambient pressure lumen 40, distal to ambient pressure port 26, is obstructed with a plug 31 of silicone rubber or similar biocompatible material. The pressure-sensing diaphragm 28 is sealingly supported on its perimeter by diaphragm support 33 made of silicone rubber or similar biocompatible material, and the only access to atmospheric side 29 of pressure-sensing diaphragm 28 being through ambient pressure lumen 40 and ambient pressure port 26. The pressure-sensing diaphragm 28 responds to a difference in pressures between sensing side 27 and atmospheric side 29; the pressure on atmospheric side 29 is substantially equal to pressure in the atmospheric pressure lumen 40, while that on sensing side 27 is substantially equal to a side pressure of a fluid stream in the central lumen 42.

Inflation of balloon 22 by injection of air or other fluid through balloon inflation lumen 38 and port 32 will cause balloon 20 to expand both radially and longitudinally, the most distal portion of balloon 20 extending more distally than Doppler ring 34. Thus, inflation of balloon 20 will effectively prevent tissue contact with Doppler ring 34, although pressure-sensing diaphragm 28 will be disposed to sense the pressure in fluid surrounding the distal catheter portion 18.

Doppler ring 34 projects ultrasonic pressure waves distal to catheter 20 to detect fluid velocity. Distally directed fluid leakage around balloon 22 of flow directed catheter 20 would alter fluid velocity distal to the catheter and thus alter the velocity detected by use of Doppler ring 34. When catheter 20 is within a vessel in which a wedge or occlusion presure is desired, optimal adjustment of inflation for balloon 22 comprises inflating the balloon 22 only until fluid velocity distal to the catheter sensed with Doppler ring 34 is zero. Further inflation is unnecessary and may be harmful.

What is claimed is:

1. A balloon catheter to measure pressure in a fluid-carrying physiological blood vessel in a patient, the catheter comprising:
    an elongated, flexible, tubular body having a proximal end, a distal end, and a circumference, having sufficient stiffness for partial insertion into the physiological blood vessel;
    a vessel occluding balloon sealingly coupled to the circumference of the catheter adjacent the distal end, said balloon having a distal edge extending beyond said distal end of said tubular body when said balloon is inflated;
    a central lumen extending through at least a portion of the tubular body from a proximal location substantially to the distal end, the central lumen having an open distal tip such that fluids or instruments may be introduced to the vessel distal to said balloon when said balloon is inflated;
    a balloon inflation lumen extending from a proximal location through at least a portion of the tubular body and communicating with the balloon for inflating and deflating the balloon;
    a pressure sensor coupled to an inner wall of the central lumen without occluding said central lumen and responding to a difference in pressures between a sensing side and an atmospheric side of said pressure sensor, said sensing side communicating with a side pressure of a fluid within said central lumen, said atmospheric side communicating with an ambient pressure pork and the pressure sensor being adjacent said distal tip of the central lumen; and
    an ambient pressure lumen extending from a proximal location through at least a portion of the tubular body and communicating with said ambient pressure port.

2. The catheter of claim 1 additionally comprising Doppler means for measuring velocity of fluid adjacent the distal end.

3. The catheter of claim 2 wherein the Doppler means is disposed on the distal end of said tubular body.

4. The catheter of claim 3 wherein the Doppler means comprises a washer-shaped ultrasonic transducer.

5. The catheter of claim 1 wherein the pressure sensor comprises a flexible pressure-sensing diaphragm.

6. The catheter of claim 5 wherein the pressure sensor additionally comprises a plurality of strain gauges communicating with said pressure-sensing diaphragm.

7. A method for determining wedge pressure within a physiological blood vessel utilizing the catheter of claim 1, comprising:
    positioning said distal end of said catheter within said physiological blood vessel;
    inflating said balloon of said catheter to occlude said physiological blood vessel; and
    measuring pressure with said pressure sensor of said catheter to determine wedge pressure within said physiological blood vessel distal to said catheter.

8. The method of claim 7, wherein said physiological blood vessel is a right pulmonary artery of a patient, and wherein said wedge pressure indicates a left atrial pressure within a patient.

9. The method of claim 7, further comprising:
    prior to said measuring step, providing for a fluid flow through said open distal tip of said central lumen to reduce the risk of clotting.

10. The method of claim 9, wherein said fluid flow is a low-flow herapin drip.

11. A method for obtaining a wedge pressure in a physiological blood vessel in a patient, the method comprising:
    positioning a distal portion of the catheter of claim 2 within the vessel;
    measuring the velocity of fluid within the vessel distal to the catheter;
    inflating the balloon only until said measured velocity of fluid within the vessel distal to the catheter is substantially zero;
    occluding the central lumen proximal to the location of the pressure sensor; and
    determining the wedge pressure at the pressure sensor.

12. A method for measuring flow rate in a physiological blood vessel in a patient, the method comprising:
    positioning a distal portion of the catheter of claim 2 within the vessel;
    measuring a fluid velocity within the vessel by Doppler means;
    measuring dimensions of the vessel by ultrasound means external to the patient; and
    calculating flow rate in the vessel from fluid velocity and vessel dimensions.

* * * * *

UNITED STATES PATENT AND TRADEMARK OFFICE
CERTIFICATE OF CORRECTION

PATENT NO.   :   5,431,628
DATED        :   July 11, 1995
INVENTOR(S)  :   Huntly D. Millar It is certified that error appears in the above-identified patent and that said Letters Patent is hereby corrected as shown below:

In claim 1, column 5, line 44, delete "pork" and insert --port;--.

Signed and Sealed this

Third Day of October, 1995

Attest:

BRUCE LEHMAN

Attesting Officer    Commissioner of Patents and Trademarks